(12) United States Patent
Verloop et al.

(10) Patent No.: US 10,260,998 B2
(45) Date of Patent: Apr. 16, 2019

(54) SAMPLING DEVICE

(71) Applicant: Kimman Process Solutions B.V., Rhoon (NL)

(72) Inventors: Pieter Charles Verloop, The Hague (NL); Erik Michiel Verloop, Rotterdam (NL)

(73) Assignee: Kimman Process Solutions B.V., Rhoon (NL)

( * ) Notice: Subject to any disclaimer, the term of this patent is extended or adjusted under 35 U.S.C. 154(b) by 335 days.

(21) Appl. No.: 15/030,312

(22) PCT Filed: Oct. 17, 2014

(86) PCT No.: PCT/NL2014/050723
§ 371 (c)(1),
(2) Date: Apr. 18, 2016

(87) PCT Pub. No.: WO2015/057070
PCT Pub. Date: Apr. 23, 2015

(65) Prior Publication Data
US 2016/0313222 A1 Oct. 27, 2016

(30) Foreign Application Priority Data
Oct. 18, 2013 (NL) .................................... 2011640

(51) Int. Cl.
*F16K 1/44* (2006.01)
*G01N 1/20* (2006.01)
*F16K 15/00* (2006.01)

(52) U.S. Cl.
CPC ............. *G01N 1/2035* (2013.01); *F16K 1/44* (2013.01); *F16K 15/00* (2013.01); *G01N 2001/205* (2013.01)

(58) Field of Classification Search
CPC .. G01N 1/2035; G01N 2001/205; F16K 1/44; F16K 15/00; F16J 15/18; F16J 15/184; F16J 15/185; F16J 15/186
See application file for complete search history.

(56) References Cited

U.S. PATENT DOCUMENTS 2,404,087 A * 7/1946 Parsons .................... G01N 1/14
137/382
2,872,817 A * 2/1959 Pitts ......................... G01N 1/14
73/224

(Continued)

OTHER PUBLICATIONS

Netherlands Patent Office, Search Report for NL2011640, dated Jun. 24, 2014.

(Continued)

*Primary Examiner* — Gilbert Y Lee
(74) *Attorney, Agent, or Firm* — Hoffmann & Baron, LLP

(57) ABSTRACT

A sampling device configured to extract a sample from a fluid flow such as an oil flow. The sampling device has a sample extraction channel to extract the sample from the fluid flow, sample extracting device configured to press a sample into the sample extraction channel, and a check valve in the sample extraction channel. The check valve has a valve seat and a sealing device movable with respect to the valve seat between a closed position, in which the sealing device sealingly engages the valve seat and an open position in which the sealing device is spaced from the valve seat to allow fluid flow between the valve seat and the sealing device. The sealing device and the valve seat may have first seal element and a second seal element to engage in the closed position with the other.

17 Claims, 4 Drawing Sheets

(56) References Cited

U.S. PATENT DOCUMENTS

| | | | |
|---|---|---|---|
| 5,743,343 A * | 4/1998 | Heller | E21B 25/00 |
| | | | 175/20 |
| 5,878,993 A | 3/1999 | St. Germain | |
| 6,216,782 B1 * | 4/2001 | Skinner | E21B 49/081 |
| | | | 166/250.01 |
| 6,776,360 B2 * | 8/2004 | Haruch | B05B 1/306 |
| | | | 239/591 |
| 2009/0267014 A1 | 10/2009 | Ishitoya et al. | |
| 2012/0291568 A1 | 11/2012 | Gransaether | |

OTHER PUBLICATIONS

Netherlands Patent Office, Written Opinion for NL2011640, dated Jun. 24, 2014.

* cited by examiner

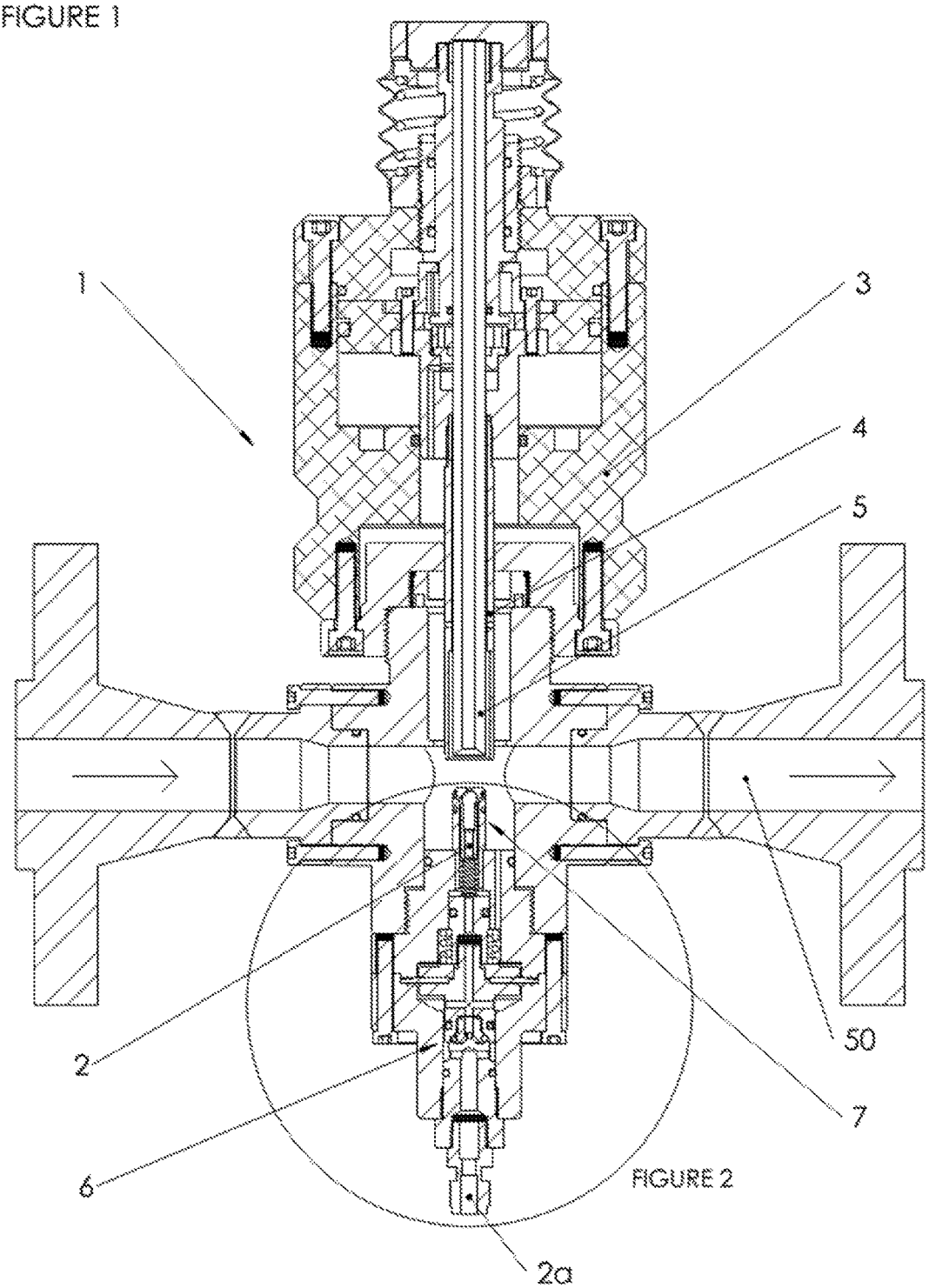

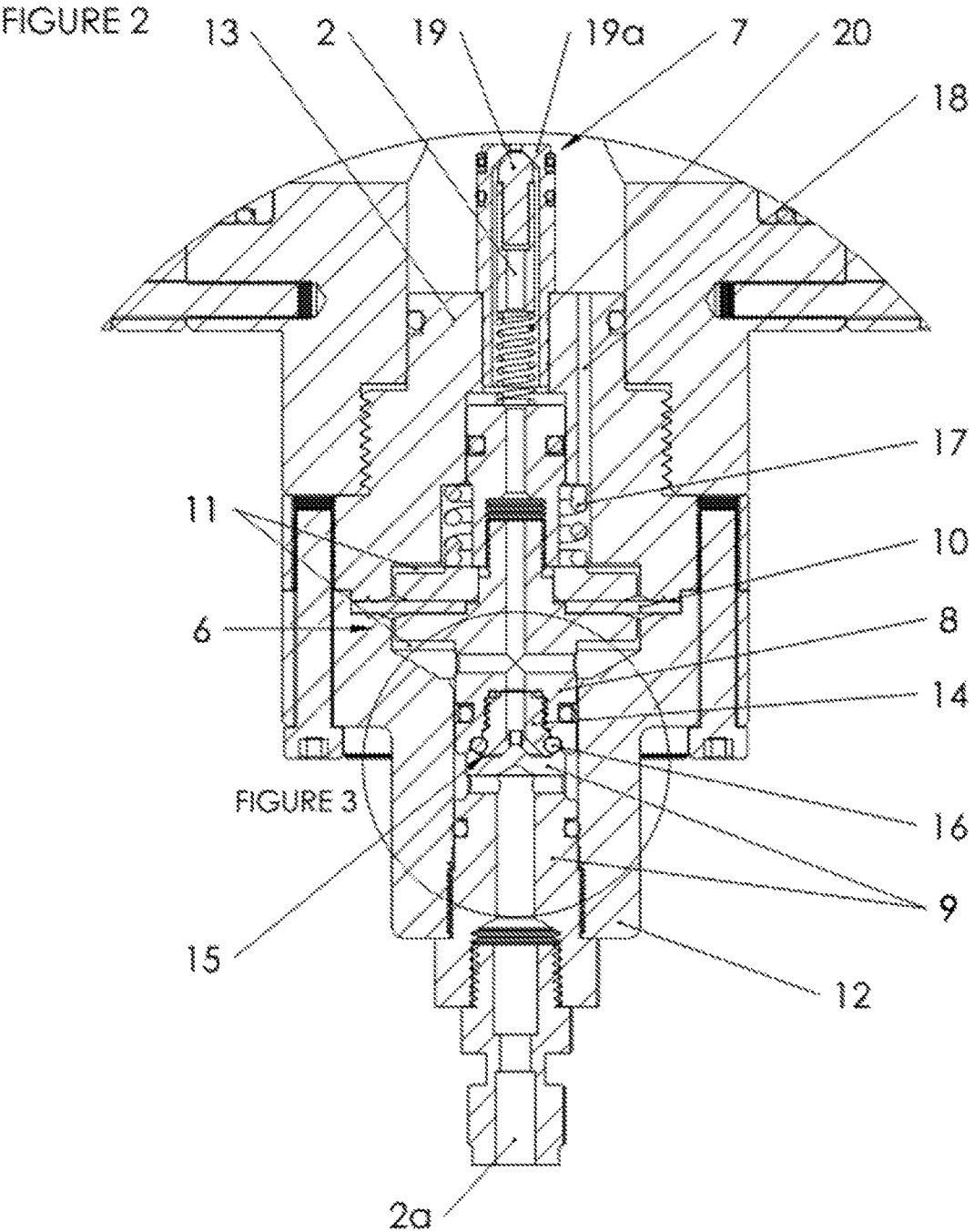

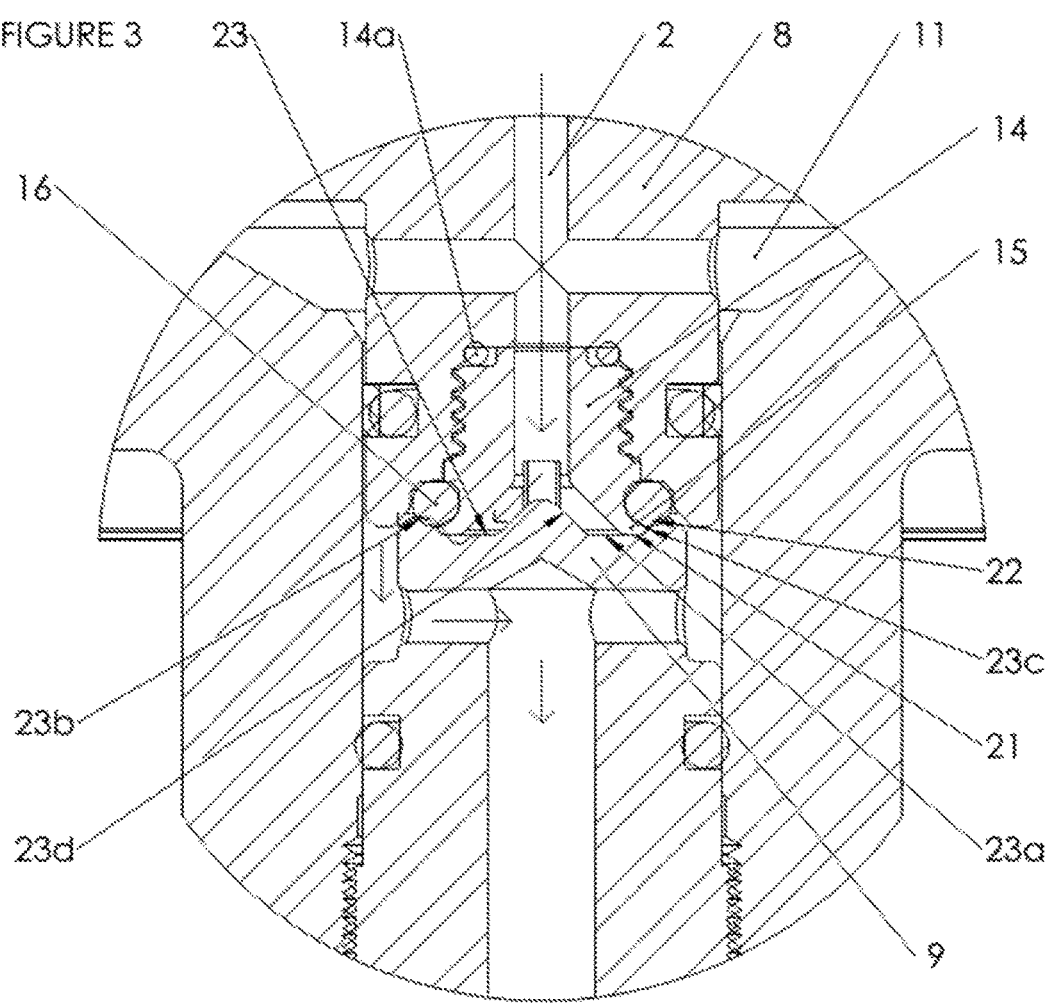

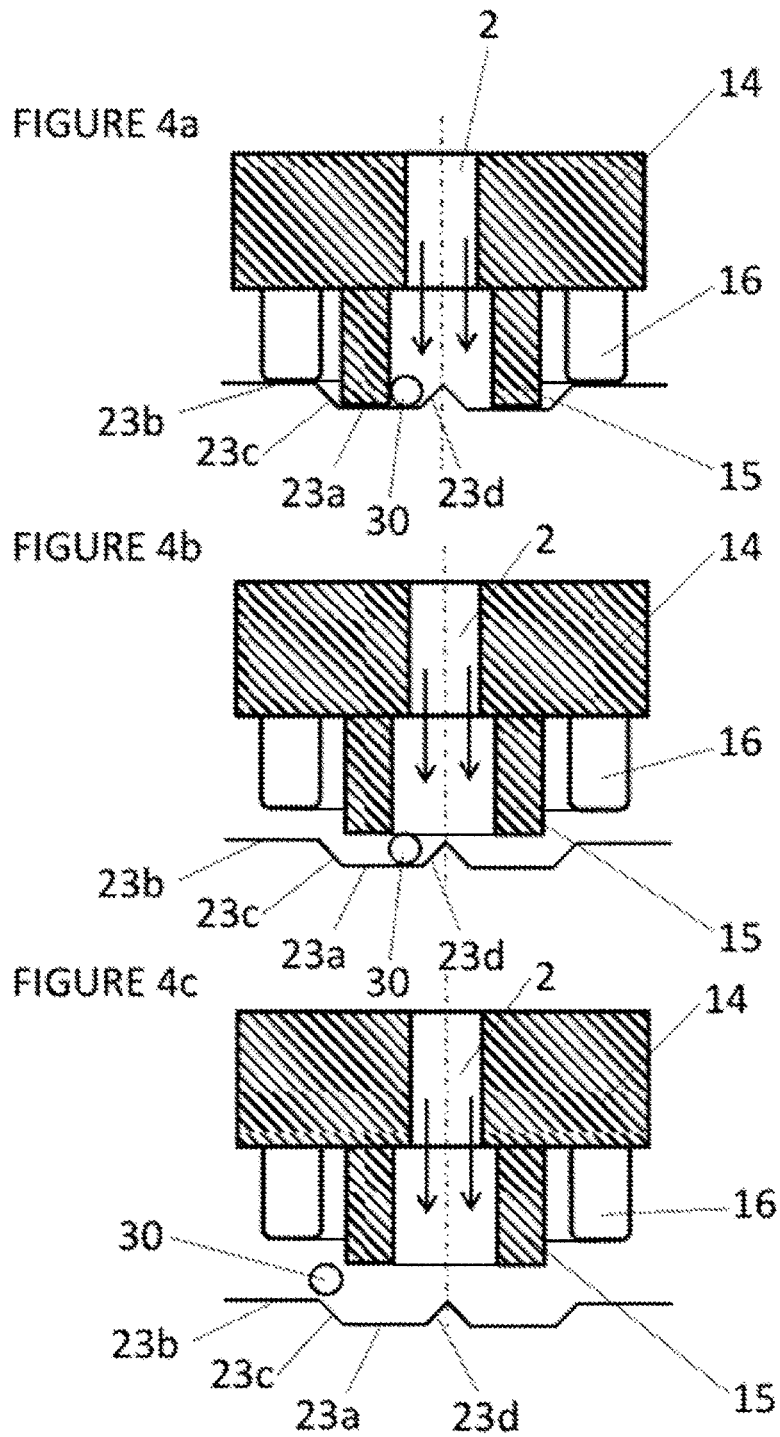

SAMPLING DEVICE

CROSS-REFERENCE TO RELATED APPLICATIONS

This application is the National Stage of International Application No. PCT/NL2014/050723 filed on Oct. 17, 2014, which claims the benefit of Netherlands Application No. NL 2011640, filed Oct. 18, 2013.

FIELD OF THE INVENTION

The present invention relates to a sampling device configured to extract a sample from a fluid flow.

BACKGROUND OF THE INVENTION

Fluid sampling is used to acquire a manageable representative collection volume of a much larger volume. Automatic liquid sampling is used when accurate samples at steady intervals are required to accurately acquire a reliable representation of the bulk volume. The sampled liquids are send to a location, most of the time a laboratory, where the volume can be analyzed and its content can be determined.

Liquid sampling devices are used over 50 years and perform a major role in the qualitative measurement, in particular in oil and gas industry. These sampling devices may for instance be mechanical operating constant volume pumps. The sampling device usually comprises a sample extraction channel in fluid communication with a main flow through a main pipeline, for example an oil pipeline. A sample can be separated from the main flow by pressing a sample in the sample extraction channel. The sample extraction channel may be provided with one or more check valves to avoid that the sample flows back into the fluid flow or that fluid undesirably enters the sample extraction channel.

A prior art sampling device is disclosed in GB2116521. This prior art sampling device comprises a pressure balanced check valve.

The check valves, in particular the sealing surfaces of the check valves are subject to wear. Especially when the liquid is not a clean pure substance but contains hard solids, like sand or has a high viscosity or pressure, the performance of the sampling device deteriorates over time. The wear of the sampling device and deterioration of its performance is mostly due to seal leakage causing sampled liquids to leak to the main fluid flow or to the environment or main flow liquid leaking into the sample volume area.

SUMMARY OF THE INVENTION

It is an object of the invention to provide a check valve for a sampling device which provides proper sealing of the sample extraction channel, but at the same time is less susceptible to wear.

The invention provides a sampling device configured to extract a sample from a fluid flow, in particular an oil flow, the sampling device comprising:

a sample extraction channel to extract the sample from the fluid flow, and a check valve in the sample extraction channel, and a sample extraction device configured to press a sample into the sample extraction channel, wherein the check valve comprises a valve seat and a sealing device movable with respect to the valve seat between a closed position, in which the sealing device sealingly engages the valve seat and an open position, in which the sealing device is spaced from the valve seat to allow fluid flow between the valve seat and the sealing device, characterized in that one of the sealing device and the valve seat comprises a first seal element and a second seal element to engage in the closed position with the other of the sealing device and the valve seat, wherein the first seal element has a first wear resistance and a first flexibility and wherein the second seal element has a second wear resistance and a second flexibility, wherein the first wear resistance is substantially larger than the second wear resistance and wherein the second flexibility is substantially larger than the first flexibility, wherein the first seal element and the second seal element are arranged adjacent to other, and wherein the first seal element is arranged upstream of the second seal element.

In accordance with the invention the check valve comprises a first seal element and a second seal element. The first seal element is arranged adjacent to and upstream of the second seal element. The first seal element has a relatively large wear resistance compared to the second seal element, while the second seal element has a relatively large flexibility compared to the first seal element.

For example, the first seal element may be a metal seal element, for example of stainless steel, and the second seal element may be a rubber or plastics seal element. Any other combination of materials for the first and second seal element, wherein the first seal element has a relatively large wear resistance, while the second seal element has a relatively large flexibility, may also be used.

In embodiments, the first seal element may for example comprise or be made of steel, stainless steel, duplex, Ni Cr alloys, tungsten carbides or any other metal or hard plastics. In an embodiment the first seal element may be provided with a coating to improve hardness and/or wear resistance.

The second seal element may comprise or be made of materials like NBR, Fluorocarbon, PEEK, PTFE, PU, PE, POM or combinations of these materials.

The flexibility of the first seal element and the second seal element may be provided by the material and/or shape of the first and second seal element. For example, the relative large flexibility of the second seal element may be obtained by a relative flexible material and/or by a flexible shape of the second seal element, for example a U-Cup or C-cup seal. In particular, in high or very high pressure applications relative soft material cannot be used, and therefore hard material, in particular metal with a flexible shape may be selected.

The wear resistance of the first seal element and the second seal element may be provided by the material and/or the flexibility of the first and second seal element. For example, the relative high wear resistance of the first seal element may be obtained by using a relative hard material and/or by using a stiff material and/or construction. In this respect it is remarked that a stiff seal element will generally be more wear resistant than a flexible seal element of the same material.

The material on which the first seal element and second element, in the closed position, sealingly engage is preferably stiff and wear resistant, and can be made of the same or a similar material as the first seal element. For example, when the first seal element and the second seal element are mounted on the valve device, the valve seat may be made of metal with a relative stiff construction.

The second seal element is, due to its flexibility, suitable to provide a fluid tight seal between the valve device and the valve seat. In the closed position, the first seal element provides a suitable blockage device for blocking particles such as grains of sand or other solid particles.

The first seal element and the second seal element may be mounted on the valve device or the valve seat, but are preferably mounted on the valve device.

When the seal device is moved to the open position, the first seal element and the second seal element on the valve device may be moved simultaneously away from the valve seat. As long as a distance between the first seal element and the valve seat is substantially smaller than a dimension of a solid particle, it will not be able to move between the first seal element and the valve seat.

When the solid particles are able to move between the first seal element and the valve seat, the second seal element has also moved a suitable distance from the valve seat. As a result, wear or damage of the relatively flexible material of the second seal element, which is more susceptible to wear, is avoided or substantially decreased.

Thus, as a result of the combination of the first seal element and the second seal element, wear of the second seal element is substantially reduced which provides a longer practical life span to the check valve.

In an embodiment, the valve seat and/or valve device are shaped to create a curved flow between the seat sealing surface and the valve device, wherein the second sealing element is arranged in an inner side of a curvature of the curved flow.

By creating a curved flow between the valve device and the valve seat, the second seal element can be placed at the inner side of the curvature of the curved flow. As a result, any wear promoting particles in the fluid flow, such as solid particles, will tend to flow at the outer side of the curvature which further reduces the chance of contact of solid particles with the second seal element.

In an embodiment, the valve seat comprises a seat sealing surface to cooperate with a first sealing surface of the first seal element and a second sealing surface of the second seal element. The seat sealing surface may comprise a recessed part, wherein, in the closed position of the valve device, the first sealing surface engages the recessed part.

In a further embodiment, the second sealing surface engages, in the closed position of the valve device, a non-recessed part of the seat sealing surface.

As a result of this construction the first sealing surface engages the valve seat at another plane, perpendicular to the direction of movement of the valve device than a plane in which the second sealing surface engages the valve seat. By providing a sealing engagement of the first and second sealing surface at different planes, the wear of the second sealing surface/second seal element may be further reduced.

In an embodiment, the plane in which second sealing surface engages the valve seat sealing surface is retracted with respect to the plane in which the first sealing surface engages the valve seat.

In an embodiment, the second sealing surface engages, in the closed position of the valve device, a rim between a recessed and a non-recessed part of the seat sealing surface. Such rim is suitable to provide a good sealing between the flexible material of the second sealing element and the valve seat.

In an embodiment, the valve device comprises a main body and a seal support element supporting the first seal element and the second seal element, wherein the seal support element is removably mounted on the main body.

A removable seal support element which supports both the first seal element and the second seal element is advantageous for seal replacement. When one or both of the first seal element and the second seal element require replacement due to wear, the seal support element including the first seal element and the second seal element may be replaced by a single action. This makes a quick and reliable replacement of the first and second seal element possible.

Generally, the sample extraction device may comprise a fluid separation device to separate fluid from the fluid flow in a main pipe, and a pressurizing device to press the separated fluid at least partly in the sample extraction channel. The fluid separation device may for example comprise an outer tube to isolate a quantity of the fluid of the main flow in fluid communication with the sample extraction channel. The pressurizing device may comprise an inner tube arranged in the outer tube that may act as piston to pressurize the isolated fluid quantity in the outer tube. The pressure may exceed a threshold closure force of the check valve so that fluid from the isolated fluid quantity can flow through the sample extraction channel towards a sample container and/or sample outlet.

In an embodiment, the check valve is a pressure balanced check valve comprising a diaphragm. Such pressure balanced check valve is very suitable to be used in a sampling device arranged to extract samples from a high pressure fluid flow, since the pressure balanced check valve may decrease stresses on the seal elements as forces are balanced and activation and control of the check valve may be more precise/accurate.

The pressure balance check valve comprises a diaphragm arranged in a pressure balancing space. One side of the diaphragm is in fluid communication with the main fluid flow, and the other side is in fluid communication with the sample extraction channel upstream of the check valve. The movement of the diaphragm is used to move the valve device between the open and closed position. The valve device is biased by a biasing device, for example by a spring, in the closed position. The valve device will only move to the open position, when the pressure in the sample extraction channel upstream of the check valve exceeds the pressure of the main fluid flow and the pressure provided by the biasing device.

In an embodiment, the sampling device comprises a second check valve in the sample extraction channel upstream of the check valve. Further check valves may be provided in the sample extraction channel. These further check valves may be of any suitable type and do not necessarily require a combination of a first seal element and a second seal element in accordance with the present invention.

The invention further relates to a check valve as discussed further herein. Such check valve may be mounted on or in a sampling device, for example connected to an outlet of a sample extraction channel as replacement of or in addition to another check valve.

BRIEF DESCRIPTION OF THE DRAWINGS

An embodiment of a sampling device according to the invention will now be described in further detail, by way of example only, with reference to the accompanying drawings, in which:

FIG. 1 shows a cross section of an embodiment of a sampling device according to the invention;

FIG. 2 shows a detail of FIG. 1;

FIG. 3 shows a further detail of FIG. 2; and

FIGS. 4a-4c show schematically an embodiment of a valve according to the invention in closed, intermediate and open position, respectively.

DETAILED DESCRIPTION OF THE INVENTION

FIG. 1 shows a sampling device configured to extract a sample from a fluid flow, in particular an oil flow. The sampling device is generally denoted by reference numeral 1. The sampling device 1 is arranged in fluid pipeline 50 through which a main flow of fluid flows.

The sampling device 1 comprises a lower part with a sample extraction channel 2 to extract and isolate a fluid sample from the fluid flow in the pipeline 50 and to guide the extracted sample to a sample outlet 2a or a sample receiving space/container. The sampling device 1 further comprises an upper part comprising a sample extraction device 3 configured to press a sample into the sample extraction channel 2.

The sample extraction device 3 comprises a tube assembly movable in a direction perpendicular to the flow direction of the main flow in the pipeline 50. The tube assembly comprises an outer tube 4 with a lower open end and an inner tube arranged in the outer tube 5 with a lower closed end.

To press a sample in the sample extraction channel 2, the outer tube 4 is moved downwards to isolate a quantity of liquid from the main flow within the outer tube 4, while the outer tube sealingly engages with an upper extension of the lower part of the sampling device 1. Then, the inner tube 5 may be moved downwards to pressurize, as a piston, the isolated liquid in the outer tube 4. This pressurized fluid may at least partly enter the sample extraction channel 2 to extract the sample from the main flow. After the sample has entered the sample extraction channel 2, the tube assembly may again be moved upwards so that the fluid flow in the pipeline 50 is not hindered by the tube assembly.

FIG. 2 shows the lower part of the sampling device 1 in more detail.

The sampling device comprises a pressure balanced check valve 6 in the sample extraction channel 2 and a second check valve 7 at the beginning of the sample extraction channel.

The pressure balanced check valve comprises a valve body 8 and a valve seat 9. The valve body 8 comprises a diaphragm 10 arranged in a pressure balance chamber 11. The circumferential edge of the diaphragm 10 is clamped between a first housing part 12 and a second housing part 13 of the check valve 6.

The valve body 8 further comprises a seal element support device 14 supporting a first seal element 15 and a second seal element 16. The first seal element 15 is integral with the seal support device 14 and for instance made of metal, for example stainless steel. The second seal element 16 is for example made of rubber and mounted in a circumferential groove of the seal support device 14. The seal element support device 14 is removably mounted in the valve body 8 such that, when desired, the seal element support device 14 with the first seal element 15 and the second seal element 16 can easily be replaced by another. A seal element 14a is provided to sealingly mount the seal element support device 14 in the valve body 8 using a screw thread connection.

The valve device 8 is movable between a closed position (as shown in FIG. 2) in which the first seal element 15 and the second seal element 16 engage the valve seat 9, and an open position, in which the sealing device is spaced from the valve seat to allow fluid flow between the valve seat 9 and the first and second seal element 15, 16.

A spring 17 is provided to bias the valve body 8 to the closed position.

The upper side of the pressure balance chamber 11, i.e. above the diaphragm 10 is in fluid communication with the pipeline 50 via fluid connection conduit 18. The lower side of the pressure balance chamber 11, i.e. below the diaphragm 10 is in fluid communication with the sample extraction channel 2 upstream of the valve seat 9 and the first and second seal element 15, 16.

As a result of this construction, the valve body 8 can only move from the closed position to the open position, when the pressure in the sample extraction channel 2/lower side of the pressure balance chamber 11 is higher than the pressure in the main pipeline 50/upper side of the pressure balance chamber and the pressure exerted by spring 17.

The second check valve 7 is of relative simple design. The second check valve 7 comprises a sealing element 19 that is biased by a second spring 20 in the closed position against a second valve seat 19a. The second check valve 7 may open by compression of the second spring 20.

FIG. 3 shows the valve seat 9 and the first seal element 15 and the second seal element 16 in more detail. The combination of the first seal element 15 and the second seal element 16 is shown in the closed position. The flow of fluid through the sample extraction channel 2 when the check valve 6 is in open position is shown by arrows.

A first sealing surface 21 of the first seal element 15 and a second sealing surface 22 of the second seal element 16 engage a seat sealing surface 23 of the valve seat 9. The first sealing surface 21 and the second sealing surface 22 are each annular and arranged concentrically with respect to each other.

The annular first sealing surface 21 has a smaller diameter than the annular second sealing surface 22 such that fluid flowing through the sample extraction channel 2 first passes the first seal element 15 before the second seal element 16.

The seat sealing surface 23 comprises a recessed part 23a, a non-recessed part 23b and a transition part 23c, connecting the recessed part 23a and the non-recessed part 23b. In the middle of the seat sealing surface 23 a cone shaped flow guiding element 23d is provided to direct the flow of fluid over the seat sealing surface 23. In the closed position of the valve body 8, the first sealing surface 21 sealingly engages with the recessed part 23a. Further, in the closed position, the second sealing surface 22 sealingly engages a rim formed by the non-recessed part 23b and the transition part 23c.

The first seal element 15 has a first wear resistance and a first flexibility and the second seal element 16 has a second wear resistance and a second flexibility. Since the first seal element 15 is made of metal and the second seal element 16 is made of rubber the first wear resistance is substantially larger than the second wear resistance and the second flexibility is substantially larger than the first flexibility. The flexibility of the second seal element may also be obtained by the shape of the second seal element. As a result of these characteristics of the first seal element 15 and the second seal element 16, the combination of the first seal element 15 and the adjacent second seal element 16 is very suitable to improve wear resistance of the check valve 6, but at the same time ensure that the check valve 6 is properly closed when the valve body 8 is in the closed position.

This wear resistance of the check valve 6 is in particular useful when the sampling device 1 is used in fluid flows comprising contamination in the form of solid particles, such as grains of sand or the like. The first seal element 15 is very suitable to block these solid particles, and is less susceptible to wear of the material of the first seal element 15. At the same time the material of the first seal element 15 is less suitable for sealing purposes due to its limited flexibility.

The relatively flexible material of the second seal element 16 is less suitable to block the solid particles and/or is more susceptible to wear, but provides very good sealing characteristics.

Since the first seal element 15 is provided adjacent to and upstream of the second seal element 16, the first seal element 15 can be used to protect the second seal element 16 from wear due to pressing of the solid particles with high pressure along the second seal element 16.

FIGS. 4*a*-4*c* show schematically the check valve in a closed position (FIG. 4*a*), intermediate position (FIG. 4*b*) and an open position (FIG. 4*c*).

In FIG. 4*a* a solid particle 30 is shown. The solid particle 30 lies against the first seal element 15. When a sample is extracted from the fluid flow by actuation of the sample extraction device 3, the valve body 8 will be moved from the closed position to the open position. As soon as the first seal element 15 and the second seal element 16 move away from the valve seat 9, fluid will flow between the valve seat 9 and the first seal element 15 and the second seal element 16 towards the outlet 2*a*. Since this first seal element 15 has a relatively large wear resistance and low flexibility, the solid particle 30 will however still be blocked by the first seal element 15, as shown in FIG. 4*b*.

As soon as the first seal element 15 is sufficiently spaced from the valve seat 9 to allow the solid particle 30 to move between the first seal element 15 and the valve seat 9, the second seal element 16 has also been moved over the same distance away from the valve seat 9. As a result, the chance that the solid particle is pressed with high pressure along the material of the second seal element 16 with a scraping effect on the material is substantially reduced, therewith decreasing the wear of the second seal element 16 due to solid particles in the fluid flow.

Further, in the embodiment of FIGS. 1-3, the second seal element 16 is positioned in the inside curvature of the curved flow caused by the shape of the seat sealing surface 23, causing any wear promoting particles in the fluid to flow at the outer curvature. This further reduces the chance of contact of the particles with the secondary seal element 16. In particular, the solid particles 30 in the fluid may roll over the seat sealing surface 23 as the flow direction is curved, allowing solid particles 30 to move along the outer curvature, keeping distance from the second seal element 16.

Also, the transition of the recessed part 23*a* to the non-recessed part 23*b* via the transition part 23*c* may have a positive effect on the wear of the second seal element 16 as the transition will shortly slow down the solid particle 30, as a result of which the second seal element 16 has more time to move away from the valve seat 9, therewith further decreasing the chance of wear of the second seal element 16.

Since the first seal element 15 and the and second seal element 16 are arranged adjacent to each other, preferably abutting each other, there is less or no possibility for solid particles to be trapped between the first seal element 15 and the second seal element 16 when the check valve 6 is closed. This further reduces the chance on wear of the check valve 6.

Hereinabove, a check valve has been described, wherein the check valve is used in a sampling device, in particular a sampling device to be used for fluid with contamination in the form of solid particles that is transported under relative high pressures. Such fluid may in particular be oil or oil like materials in which solid particles such as grains of sand are present. The construction of the check valve according to the invention may increase substantially the wear resistance of the check valve. The check valve may be provided as a separate part connected to the sample extraction channel.

The construction of the check valve may however also be applied in other applications in which the wear resistance of the check valve should be increased without reducing the sealing characteristics of the check valve.

The invention claimed is:

1. A fluid flow sampling device configured to extract a sample from a fluid flow such as an oil flow, the sampling device comprising:
   a sample extraction channel to extract the sample from the fluid flow;
   a sample extraction device configured to press a sample into the sample extraction channel; and
   a check valve in the sample extraction channel, the check valve having a valve seat and a sealing device movable with respect to the valve seat between a closed position, in which the sealing device sealingly engages the valve seat, and an open position, in which the sealing device is spaced from the valve seat to allow fluid flow between the valve seat and the sealing device,
   wherein selectively one of the sealing device and the valve seat comprises a first seal element and a second seal element to engage in the closed position with the other of the sealing device and the valve seat, the first seal element arranged adjacent the second seal element, and the first seal element arranged upstream of the second seal element,
   wherein the first seal element has a first wear resistance and a first flexibility and second seal element has a second wear resistance and a second flexibility, the first wear resistance substantially higher than the second wear resistance and the second flexibility substantially larger than the first flexibility, and
   wherein, when the sealing device is moved to the open position, the first seal element and the second seal element are moved simultaneously away from the seat.

2. The sampling device of claim 1, wherein the first seal element has a first sealing surface and the second seal element has a second sealing surface.

3. The sampling device of claim 2, wherein the first sealing surface is annular and the second sealing surface is annular.

4. The sampling device of claim 3, wherein the first annular sealing surface and the second annular sealing surface are substantially concentric.

5. The sampling device of claim 4, wherein the first annular sealing surface has a smaller diameter than the second annular sealing surface.

6. The sampling device of claim 5, wherein the valve seat and/or valve device are shaped to create a curved flow between the seat sealing surface and the valve device, and the second sealing element is arranged in an inner side of a curvature of the curved flow.

7. The sampling device of claim 6, wherein the sealing device comprises the first seal element and the second seal element, and wherein the valve seat comprises a seat sealing surface to cooperate with the first sealing surface and the second sealing surface.

8. The sampling device of claim 7, wherein the seat sealing surface comprises a recessed part and a non-recessed part, and further wherein, in the closed position of the valve device, the first sealing surface engages the recessed part and the second sealing surface engages the non-recessed part of the seat sealing surface.

9. The sampling device of claim 8, wherein, in the closed position of the valve device, the second sealing surface engages a rim between a recessed and a non-recessed part of the seat sealing surface.

10. The sampling device of claim 2, wherein the first sealing surface of the first seal element and the second sealing surface of the second seal element substantially abut against each other.

11. The sampling device of claim 10, wherein the first seal element comprises a metal and wherein the second seal element comprises a rubber material.

12. The sampling device of claim 11, wherein the valve device comprises a main body and a seal support element supporting the first seal element and the second seal element, and wherein the seal support element is removably mounted on the main body.

13. The sampling device of claim 1, wherein the check valve is a pressure balanced check valve comprising a diaphragm.

14. The sampling device of claim 1, wherein the second flexibility of the second seal element is obtained by the material and/or shape of the second seal element.

15. The sampling device of claim 1, wherein the sample extraction device comprises a fluid separation device to separate fluid from the fluid flow, and a pressurizing device to press the separated fluid at least partly in the sample extraction channel.

16. The sampling device of claim 15, wherein the sampling device comprises a second check valve in the sample extraction channel upstream of the check valve.

17. A check valve for use in connection with a fluid flow sampling device, the check valve comprising a valve seat and a sealing device movable with respect to the valve seat between a closed position, in which the sealing device sealingly engages the valve seat and an open position, in which the sealing device is spaced from the valve seat to allow fluid flow between the valve seat and the sealing device, one of the sealing device and the valve seat comprising a first seal element and a second seal element to engage in the closed position with the other of the sealing device and the valve seat,
  wherein the first seal element has a first wear resistance and a first flexibility and wherein the second seal element has a second wear resistance and a second flexibility, the first wear resistance substantially larger than the second wear resistance and the second flexibility substantially larger than the first flexibility,
  wherein the first seal element and the second seal element are arranged adjacent to other, and the first seal element is arranged upstream of the second seal element with respect to an intended flow direction through the check valve, and
  wherein, when the sealing device is moved to the open position, the first seal element and the second seal element are moved simultaneously away from the seat.

* * * * *